US00PP28175P2

(12) United States Plant Patent
Pan

(10) Patent No.: US PP28,175 P2
(45) Date of Patent: Jul. 11, 2017

(54) ***LANTANA* PLANT NAMED 'LANZ0008'**

(50) Latin Name: ***Lantana camara* L.**
Varietal Denomination: LANZ0008

(71) Applicant: SYNGENTA PARTICIPATIONS AG, Basel (CH)

(72) Inventor: Shifeng Pan, Gilroy, CA (US)

(73) Assignee: Syngenta Participations AG, Basel (CH)

( * ) Notice: Subject to any disclaimer, the term of this patent is extended or adjusted under 35 U.S.C. 154(b) by 75 days.

(21) Appl. No.: 14/545,557

(22) Filed: May 20, 2015

(51) Int. Cl.
*A01H 5/02* (2006.01)

(52) U.S. Cl.
USPC ..... Plt./227

(58) Field of Classification Search
USPC ..... Plt./227
See application file for complete search history.

*Primary Examiner* — Anne Grunberg
(74) *Attorney, Agent, or Firm* — Dale Skalla

(57) ABSTRACT

A new *Lantana* plant named 'LANZ0008' particularly distinguished large sized, cream yellow to pink flowers with an yellow throat, dark green foliage, early flowering and excellent floriferousness, spreading plant habit and good heat tolerance compared to control.

1 Drawing Sheet

Latin name of the genus and species of the plant claimed: *Lantana camara* L.

Varietal denomination: 'LANZ0008'.

BACKGROUND OF THE NEW PLANT

The present invention comprises a new *Lantana*, botanically known as *Lantana camara* L., and hereinafter referred to by the variety name 'LANZ0008'.

'LANZ0008' is a product of a planned breeding program. The new cultivar 'LANZ0008' has large sized, cream yellow to pink flowers with a yellow throat, dark green foliage, early flowering and excellent floriferousness, spreading habit and good heat tolerance.

'LANZ0008' originates from the cross-pollination between 'G302-1' and 'G527-3' made in July 2009 in a greenhouse in Gilroy, Calif., USA. The female parent 'G302-1' has white flower color, a spreading plant habit, medium size plant and displays smaller growth than 'LANZ0008'.

The male parent 'G527-3' has a cherry flower color, a bushy plant habit, early flowering, and displays smaller growth than 'LANZ0008'.

The resulting seed was sown in June 2010 in a greenhouse in Gilroy, Calif. 'LANZ0008' was selected as one flowering plant within the progeny of the stated cross in November 2010.

The first act of asexual reproduction of 'LANZ0008' was accomplished when vegetative tip cuttings were propagated from the initial selection in December 2010 in a greenhouse in Gilroy, Calif.

BRIEF SUMMARY OF INVENTION

Horticultural examination of plants grown from cuttings of the plant initiated in the spring of 2011 in Gilroy, Calif., and continuing thereafter, has demonstrated that the combination of characteristics as herein disclosed for 'LANZ0008' are firmly fixed and are retained through successive generations of asexual reproduction.

'LANZ0008' has not been observed under all possible environmental conditions. The phenotype may vary significantly with variations in environment such as temperature, light intensity, and day length.

A Patent or Plant Breeder's Right for this cultivar was not yet applied.

The following traits have been repeatedly observed and are determined to be basic characteristics of the new variety. The combination of these characteristics distinguishes this *Lantana* as a new and distinct variety.

BRIEF DESCRIPTION OF THE PHOTOGRAPHS

The accompanying photographic drawings show typical flower and foliage characteristics of 'LANZ0008' with colors being as true as possible with an illustration of this type.

Figure 1:
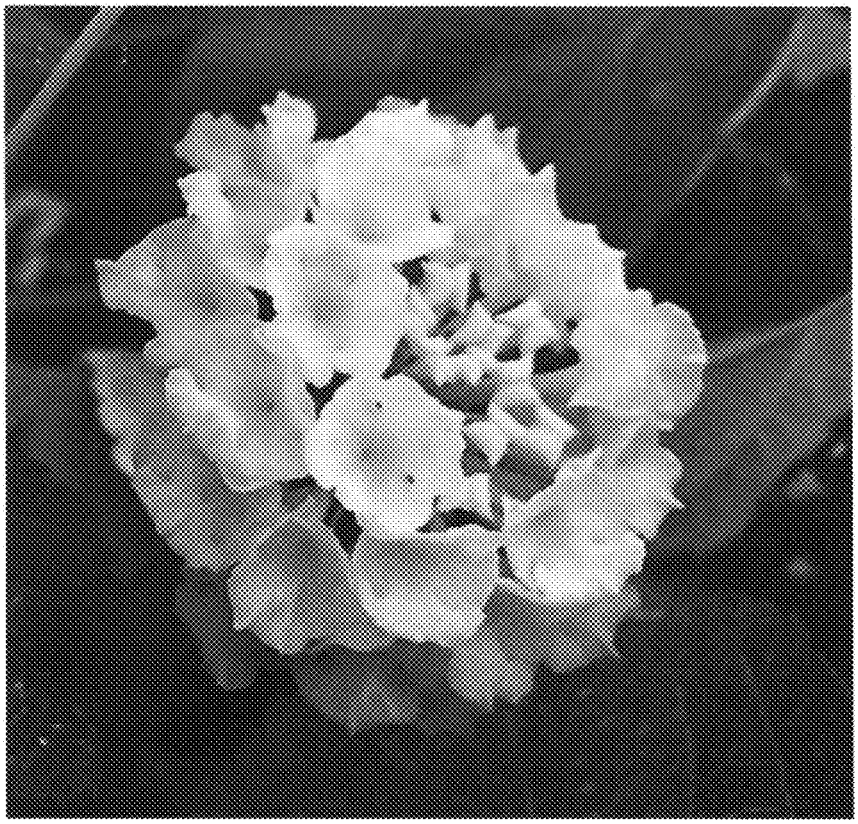
Figure 2:
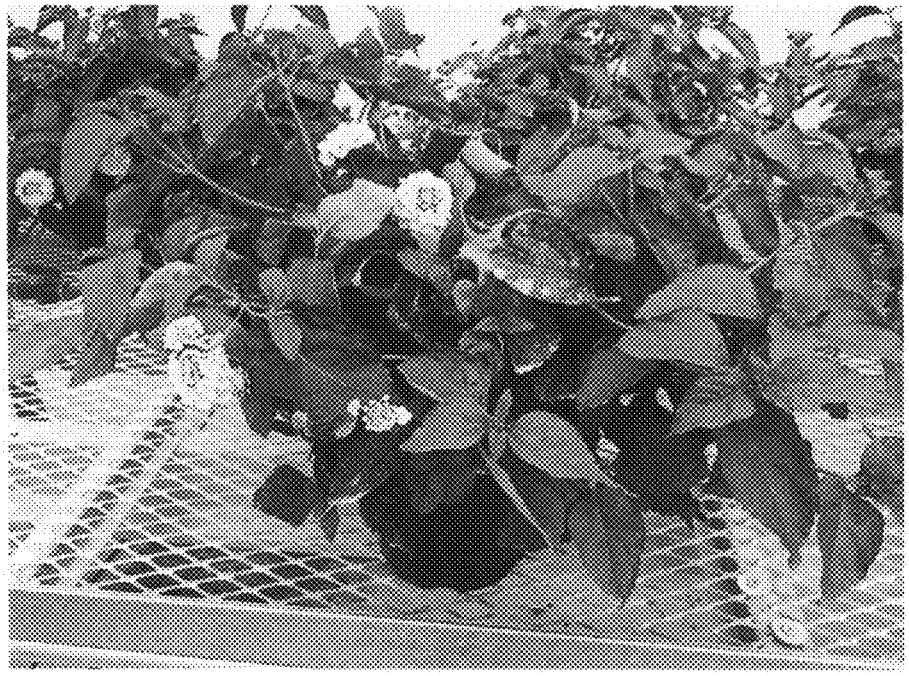

The photographic drawings show in FIG. 1 a close view of an inflorescence, and in FIG. 2 a whole flowering plant.

DETAILED BOTANICAL DESCRIPTION

The plant descriptions and measurements were taken Gilroy, Calif. in early May 2015. The plants were approximately 6 months old and were growing in 1 gallon pots in a greenhouse.

The aforementioned photographs show those same plants as used for the description. They were taken in Gilroy, Calif. on May 5, 2015 and show 6 month old plants from an indoor trial.

Color references are made to The Royal Horticultural Society Colour Chart (R.H.S.) 2001.

TABLE 1

DIFFERENCES BETWEEN THE NEW VARIETY 'LANZ0008' AND A MOST SIMILAR VARIETY

| | 'LANZ0008' | 'BALANDROGLIM', also known as 'Landmark Rose Glow' (U.S. Plant Pat. No. 18,555) |
|---|---|---|
| Internode length: | 5.1-8.0 cm | Shorter, 2.6-3.5 cm |
| Main flower color: | Cream yellow to pink | Cream yellow with lighter tones of pink |

TABLE 1-continued

| DIFFERENCES BETWEEN THE NEW VARIETY 'LANZ0008' AND A MOST SIMILAR VARIETY | | |
|---|---|---|
| | 'LANZ0008' | 'BALANDROGLIM', also known as 'Landmark Rose Glow' (U.S. Plant Pat. No. 18,555) |
| Plant habit: | Wide, flat spreading growth | Semi-upright growth habit |

Plant:

*Form, growth and habit.*—Semi-woody, grown as an annual or perennial; spreading habit; well branched.
*Plant height.*—28-32.0 cm.
*Plant height (inflorescence included).*—29-33.0 cm.
*Plant width.*—34-38.0 cm.

Foliage:

*Type.*—Opposite.
*Immature, leaf color, upper surface.*—Closest to RHS 137A.
*Immature leaf color, lower surface.*—Closest to RHS 137C.
*Mature, leaf color, upper surface.*—Closest to RHS 139A.
*Mature, leaf color, lower surface.*—Closest to RHS 147B.
*Length.*—8.5-9.5 cm.
*Width.*—5.3-5.9 cm.
*Shape.*—Elliptic.
*Base shape.*—Rounded.
*Apex shape.*—Acute.
*Margin.*—Dentate.
*Texture, upper.*—Hirsute.
*Lower surface.*—Hirsute.
*Lower surface.*—RHS 147B.
*Pattern of veining.*—Pinnate.
*Petioles color.*—RHS 137C.
*Petioles length.*—0.4-0.9 cm.
*Diameter of petiole.*—0.2-0.3 cm.
*Texture (upper and lower surface).*—Hirsute with some very short glandular hairs.

Stem:

*Color of stem.*—RHS 147B.
*Length of stem.*—17-19.0 cm.
*Diameter.*—0.50 cm.
*Length of internodes.*—5.1-8.0 cm.
*Texture.*—Pilose, hirsute.

Inflorescence:

*Type.*—Umbel like, flattened semi-sphere, the florets are sessile on an ovate receptacle.
*Blooming habit.*—Flowers continuously from spring through fall.
*Number of open flowers per inflorescence.*—38-42.
*Quantity of inflorescences per plant.*—About 10 (with open florets).
*Lastingness of individual blooms on the plant.*—About 4 weeks (depending on temperatures).
*Fragrance.*—Slightly spicy.
*Umbel horizontal diameter.*—About 4.5 cm.
*Umbel vertical height.*—1.5-2.2 cm.
*Peduncle color.*—RHS 146C.
*Length of peduncle.*—2.1-2.6 cm.
*Peduncle diameter.*—0.15 cm.
*Texture.*—Hirsute, glandular hairs.

Flower:

*Floret form.*—Corolla salver-shaped to shallow cup-shaped, with a relatively long tube at the base; each flower subtended by a single bract.
*Length of floret.*—1.8-2.4 cm.
*Width of floret.*—0.9-1.4 cm.
*Depth of floret.*—0.9-1.4 cm.
*Young floret, color upper surface.*—RHS 3D and RHS 15B.
*Young floret, color lower surface.*—RHS 16D.
*Mature florets, color upper surface.*—RHS 72C outer petal and RHS 15A near throat.
*Mature floret, color lower surface.*—RHS 63C overlain with RHS 8D.
*Apex shape.*—Rounded.
*Degree of lobation.*—Moderate.
*Margin.*—Crenate.
*Base.*—Fused.
*Texture, upper surface.*—Papillose.
*Lower surface.*—Papillose.
*Tube, color outer surface.*—Closest to RHS 63D.
*Tube, color inner surface.*—Closest to RHS 16A.
*Tube, length.*—1.3 cm.
*Tube, diameter (at opening).*—0.15 cm.
*Tube, texture outer surface.*—Pubescent.
*Inner surface.*—Hirsute.

Bud (just before opening):

*Color.*—RHS 15D.
*Length.*—0.9-1.3 cm.
*Width.*—0.2-0.4 cm at the apex.
*Shape.*—Tubular with a flared apex.

Bract:

*Color.*—Closest to RHS 146C.
*Length.*—0.6-0.8 cm.
*Diameter.*—0.15-0.2 cm.
*Texture, upper surface.*—Hirsute.
*Texture, lower surface.*—Hirsute.

Calyx:

*Number of sepals.*—5, fused sepals forming a short tube around the base of the floret.
*Color of sepals.*—RHS 138D.
*Length of sepals.*—0.3 cm.
*Width of sepals.*—0.2 cm.
*Apex shape.*—Acuminate.
*Apex margins.*—Entire.
*Texture, outer surface.*—Pubescent.
*Inner surface.*—Glabrous.

Reproductive organs:

*Gynoecium.*—Pistil quantity: One. Length: 0.5 cm. Style color: RHS 145D. Style length: 0.3 cm. Stigma color: RHS 145A. Ovary color: RHS 146B. Ovary length: 0.1 cm. Ovary diameter: 0.1 cm.
*Androecium.*—Stamen quantity: 4. Color of filaments: RHS 16A. Length filaments: 0.15-0.2 cm. Anther color: RHS 164B. Length of anthers: 0.1 cm. Color of pollen: RHS 10B. Pollen amount: Normal.
*Fertility/seed set.*—Has not been determined to date.
*Disease/pest resistance.*—Has not been determined to date.

What is claimed is:

1. A new and distinct variety of *Lantana* plant named 'LANZ0008' substantially as illustrated and described herein.

* * * * *